US008877158B2

(12) United States Patent
Nakamura et al.

(10) Patent No.: US 8,877,158 B2
(45) Date of Patent: Nov. 4, 2014

(54) TARGETING AGENT TO NEWLY FORMED BLOOD VESSELS

(75) Inventors: Kentaro Nakamura, Ashigarakami-gun (JP); Yasuhiko Tabata, Kyoto (JP)

(73) Assignees: FUJIFILM Corporation, Tokyo (JP); Kyoto University, Kyoto (JP)

(*) Notice: Subject to any disclaimer, the term of this patent is extended or adjusted under 35 U.S.C. 154(b) by 0 days.

(21) Appl. No.: 13/377,788

(22) PCT Filed: Jun. 11, 2010

(86) PCT No.: PCT/JP2010/059917
§ 371 (c)(1),
(2), (4) Date: Dec. 12, 2011

(87) PCT Pub. No.: WO2010/143708
PCT Pub. Date: Dec. 16, 2010

(65) Prior Publication Data
US 2012/0156132 A1    Jun. 21, 2012

(30) Foreign Application Priority Data

Jun. 12, 2009  (JP) ................................. 2009-140757

(51) Int. Cl.
| | | |
|---|---|---|
| A61K 51/00 | (2006.01) | |
| A61M 36/14 | (2006.01) | |
| A61K 49/00 | (2006.01) | |
| A61B 5/00 | (2006.01) | |
| A61B 5/055 | (2006.01) | |
| A61K 49/04 | (2006.01) | |
| A61K 38/39 | (2006.01) | |
| A01N 25/00 | (2006.01) | |
| A61K 51/08 | (2006.01) | |
| C07K 14/78 | (2006.01) | |
| A61K 47/48 | (2006.01) | |

(52) U.S. Cl.
CPC ............... *C07K 14/78* (2013.01); *A61K 51/088* (2013.01); *A61K 38/39* (2013.01); *A61K 49/0002* (2013.01); *A61K 51/082* (2013.01); *A61K 47/48238* (2013.01)
USPC ........... 424/1.69; 424/9.1; 424/9.6; 424/9.34; 424/9.4; 424/9.42; 514/17.2; 514/774

(58) Field of Classification Search
None
See application file for complete search history.

(56) References Cited

U.S. PATENT DOCUMENTS

| | | | | |
|---|---|---|---|---|
| 5,773,249 A | * | 6/1998 | Cappello et al. ............. | 435/69.1 |
| 6,992,172 B1 | | 1/2006 | Chang et al. | |
| 2003/0194373 A1 | * | 10/2003 | Fauconnier et al. ......... | 424/1.69 |
| 2003/0211165 A1 | | 11/2003 | Vogel et al. | |
| 2006/0241032 A1 | * | 10/2006 | Bouwstra et al. ............ | 514/12 |

FOREIGN PATENT DOCUMENTS

| | | | |
|---|---|---|---|
| JP | 61-229816 A | | 10/1986 |
| JP | 2002-520044 A | | 7/2002 |
| JP | 2002-522504 A | | 7/2002 |
| JP | 2003-528130 A | | 9/2003 |
| WO | WO 00/04052 A2 | | 1/2000 |
| WO | WO 00/09143 A1 | | 2/2000 |
| WO | WO 01/72281 A2 | | 10/2001 |
| WO | WO 2005/079859 A1 | | 9/2005 |
| WO | WO 2006091099 A2 | * | 8/2006 |
| WO | WO 2008/103041 A1 | | 8/2008 |

OTHER PUBLICATIONS

Khew, S.T., et al., "Enzymatically crosslinked collagen-mimetic dendrimers that promote integrin-targeted cell adhesion", 2008, Biomaterials, pp. 3034-3045.*
Li., Z., et al., "64Cu-Labeled Tetrameric and Octameric RGD Peptides for Small-Animal PET of Tumor $\alpha v\beta 3$ Integrin Expression", 2007, JNM, pp. 1162-1171.*
Wu, Y., et al., "Near-Infrared Fluorescence Imaging of Tumor Integrin $\alpha v\beta 3$ Expression with Cy7-Labeled RGD Multimers", 2006, Molecular Imaging and Biology, pp. 226-236.*
Ye, Y., et al., "Design, Synthesis, and Evaluation of Near Infrared Fluorescent Multimeric RGD Peptides for Targeting Tumors", 2006, J. Med. Chem., pp. 2268-2275.*
Jonas Emsley et al, "Structure of te Integrin a2B1-binding Collagen Peptide", J. Mol. Biol, 2004, pp. 1019-1028, vol. 335.
Michael A. Dechantsreiter et al., "N-Methylated Cyclic RGD Peptides as Highly Active and Selective avB3 Integrin Antagonists", J. Med. Chem., 1999, pp. 3033-3040, vol. 42.
Shuang Liu, "Radiolabeled Multimeric Cyclic RGD Pedtides as Integrin avB3 Targeted Radiotracers for Tumor Imaging", Molecular Pharmaceutics, 2006, pp. 472-487, vol. 3, No. 5.
Vadim Pedchenko et al., "avB3 and avB5 Integrins Bind Both the Proximal RGD Site and Non-RGD Motifs within Noncollagenous (NC1) Domain of the a3 Chain of Type IV Collagen", The Journal of Biological Chemistry, Jan. 23, 2004, pp. 2772-2780, vol. 279, No. 4.
Yohei Maeshima et al., "Extracellular Matrix-derived Peptide Binds to avB3 Integrin and Inhibits Angiogenesis", The Journal of Biological Chemistry, Aug. 24, 2001, pp. 31959-31968, vol. 276, No. 34.
Yoshinori Miyahara et al., "Control of Neovascularization by Cell-Gene Hybrid Therapy and Visualization of Angiogenic Vessels by Micro-Angiographic System", Biotherapy, Sep. 2004, pp. 449-456, vol. 18, No. 5.
International Preliminary Report on Patentability issued Dec. 22, 2011, in International Application No. PCT/JP2010/059917.
Written Opinion issued Sep. 14, 2010, in International Application No. PCT/JP2010/059917.
Official Action issued in corresponding Japanese Patent Application No. 2011-518581, dated Oct. 29, 2013.

* cited by examiner

*Primary Examiner* — Michael G Hartley
*Assistant Examiner* — Lance Rider
(74) *Attorney, Agent, or Firm* — Sughrue Mion, PLLC

(57) ABSTRACT

It is an object of the present invention to provide a targeting agent that enables drug delivery to a neovascular site and the imaging of such a neovascular site, utilizing the effect of the agent to accumulate in the neovascular site. The present invention provides a targeting agent to a neovascular site, which comprises a gelatin-like protein.

11 Claims, 8 Drawing Sheets

Evaluation of "leg ischemia → neovascularization" model using laser Doppler blood-flowmeter Blood flow ratio between treated leg and untreated leg $^{125}$I labeling of R-Gel Percentage of R-Gel remaining in body R-Gel blood clearance Imaging of neovascular sites in bFGF-induced neovascular models Elimination rate from neovascular site Inhibition of accumulation of R-Gel in newly formed blood vessel with cyclo-RGDfK Imaging of tumor sites and neoplastic neovascular sites in cancer-bearing animals Accumulation in tumor and neoplastic neovascular sites HUVEC adhesiveness test HUVEC adhesiveness test-2

Photos of HUVECs on plates coated with various proteins

Comparison of 1-cell area for HUVEC cells on plates coated with various proteins Inhibition of HUVEC adhesion caused by the anti-αV antibody

US 8,877,158 B2

TARGETING AGENT TO NEWLY FORMED BLOOD VESSELS

CROSS REFERENCE TO RELATED APPLICATIONS

This application is a National Stage of International Application No. PCT/JP2010/059917 filed on Jun. 11, 2010, which claims priority from Japanese Patent Application No. 2009-140757 filed Jun. 12, 2009, the contents of all of which are incorporated herein by reference in their entirety.

TECHNICAL FIELD

The present invention relates to a targeting agent to newly formed blood vessels that uses a gelatin-like protein.

BACKGROUND ART

The term "angiogenesis" mainly refers to a phenomenon in which newly formed blood vessels are formed from existing blood vessels. Examples of normal and physiological angiogenesis include angiogenesis in fetal life and angiogenesis involved in formation of the endometrium/corpus luteum, wound healing, or the like. On the other hand, it has been known that pathologic angiogenesis is deeply associated with the growth or metastasis of a solid tumor, chronic inflammation such as diabetic retinopathy or rheumatoid arthritis, and the like. In particular, tumoral angiogenesis has been vigorously studied from both sides of treatment and diagnosis. It has been considered that a tumor having a diameter of 1 to 2 mm can obtain oxygen or nutrient as a result of diffusion from existing blood vessels. However, for a further growth, angiogenesis is essential. In the case of healthy adults, since such an event as angiogenesis occurs only at a limited site in a limited situation, it is anticipated that a therapeutic agent or imaging agent targeting against tumoral angiogenesis can becomes a tumor-specific and universal agent and/or diagnostic agent.

At present, in the diagnosis of a tumor, PET (positron emission tomography) diagnosis using FDG (fluorodeoxyglucose) is carried out on a tumor site. However, such FDG only targets to a cell and/or tissue site having high glucose-metabolizing activity, and thus its tumor specificity is not sufficient. Since FDG highly accumulates even in the brain, heart, liver and the like as a result of physiological accumulation, it is problematic in that it may be difficult for FDG to carry out tumor diagnosis in some cases. In addition, in the urinary system such as the kidney, ureter or bladder, background increases as a result of a large amount of FDG discharged into urine, and thus it is difficult to make a diagnosis. Thus, targeting that is not mediated by sugar metabolism but mediated by another mechanism, and a targeting agent mainly targeting against angiogenesis has been developed.

On the other hand, application of an angiogenic event to treatments has been carried out as an angiogenic treatment. The importance of angiogenesis has been elucidated in wound healing or a therapeutic method for ischemic disease, or in treatments that are broadly called regenerative medicine, such as organ regeneration, cell transplantation, or the reinforcement of natural healing effects. Angiogenesis exhibits therapeutic effects by itself, or angiogenesis reinforces therapeutic effects. Accordingly, it is anticipated that a therapeutic agent, a targeting agent, and/or an imaging agent, which target against angiogenesis, can be used as an agent, a diagnostic agent, and/or a means for evaluating therapeutic effects in various treatments and regenerative medicines.

In particular, in the field of regenerative medicine, there have been a few methods for thoroughly analyzing therapeutic effects, and the authenticity of the therapeutic effects has only been indirectly evaluated by a combination of existing diagnostic methods. As described above, angiogenesis plays an important role particularly in regenerative medicine, but there are only a few methods of dividing newly formed blood vessels from existing blood vessels and evaluating them. It has been particularly strongly desired to develop an imaging means for visualizing only newly formed blood vessels. However, an imaging agent has various problems such as lack of specificity to newly formed blood vessels or lack of persistency, and consequently, sufficient results have not yet been obtained.

As a means for targeting against angiogenesis, a targeting agent and/or an imaging agent targeting to $\alpha_v\beta_3$ integrin, which is reported to be expressed at a high level in endothelial cells (and some tumor cells) during angiogenesis, has been under development. The $\alpha_v\beta_3$ integrin recognizes a peptide (RGD) consisting of a sequence of arginine-glycine-aspartic acid. Thus, on the basis of the RGD sequence, various circular RGD analog compounds or circular RGD-containing peptides have been particularly developed. For example, there are present many compounds such as cyclo-RGDfK, cyclo-RGDyV, cyclo-RGDfY and cyclo-RGDyK, which were produced from a circular pentapeptide, c-RGDfV, as a lead compound, which had been developed by Kessler et al. of Munchen Institute of Technology (Non Patent Document 1).

However, since the aforementioned circular RGD compound is rapidly discharged from the body mainly by renal excretion after it has been administered, its retention time in the body is short. Accordingly, when this compound is used as a targeting agent such as a drug delivery agent or an imaging agent, it is problematic in that a time in which its targeting ability can be utilized is short, and in that a majority of the compound is discharged from the body before it reaches a target site. Meanwhile, in the imaging of newly formed blood vessels, imaging and diagnosis, since a targeting agent is labeled with a probe such as a fluorescent dye or a radioisotope, it is required from the viewpoint of safety that a signal disappears as soon as possible after completion of detection and/or diagnosis of the target site, namely, that the targeting agent disappears from the target site at an early point after completion of diagnosis. However, even if the circular RGD peptide has reached a target site, it forms a strong bond with integrin which is expressed in newly formed blood vessels. Thus, the circular RGD peptide has been problematic in that it takes a long period of time until a signal disappears from a neovascular site in some cases. As a result, it has been desired to develop an imaging material, "the retention time of which in the body is long" and "in which a signal quickly disappears from the neovascular site."

Meanwhile, biopolymers such as gelatin have been widely used as medical materials to date. However, it has not been known that such biopolymers can be used for the imaging of newly formed blood vessels. Along with the advancement of gene engineering techniques in recent years, protein synthesis by introduction of genes into *Escherichia coli* or yeast has been in progress. With the use of such techniques, various types of recombinant collagen-like proteins have been synthesized (e.g., Patent Documents 1 and 2). The synthetic proteins are non-infectious and thus superior to naturally occurring gelatins. In addition, the proteins are homogenous and have predetermined sequences and thus they can be precisely designed in terms of strength and degradability. Therefore, the use of such proteins is advantageous. However, in view of the use of recombinant gelatins suggested in the past, recombinant gelatins have been used as a replacement of naturally occurring gelatin. Needless to say, the use of recombinant gelatins as neovascular imaging agents has been unknown.

PRIOR ART DOCUMENTS

Patent Documents

Patent Document 1: U.S. Pat. No. 6,992,172
Patent Document 2: International Publication WO2008/103041

Non Patent Literature

Non Patent Document 1: MA Dechantsreiter et al. N-Methylated Cyclic RGD Peptides as Highly Active and Selective αVβ3 Integrin Antagonists. J. Med. Chem. 1999. 42: 3033-3040

SUMMARY OF INVENTION

Object to be Solved by the Invention

It is an object to be solved by the present invention to provide a targeting agent that enables drug delivery to a neovascular site and the imaging of such a neovascular site, utilizing the effect of the agent to accumulate in the neovascular site. Moreover, it is another object to be solved by the present invention to provide the above-described targeting agent, which is characterized in that it has a blood retention property higher than that of a commonly studied circular RGD compound and in that its stay in a neovascular site is short.

Means for Solving the Object

As a result of intensive studies to achieve the aforementioned objects, the present inventors have found that a gelatin-like protein having an amino acid sequence derived from a partial amino acid sequence of collagen, such as a recombinant gelatin, accumulates at an angiogenesis site, so that the inventors have found that it is possible to provide a targeting agent that enables drug delivery to a neovascular site and the imaging of such a neovascular site, utilizing the effect of the agent to accumulate in the neovascular site. This has led to the completion of the present invention.

Thus, the present invention provides a targeting agent to a neovascular site, which comprises a gelatin-like protein.

Preferably, the targeting agent of the present invention is an imaging agent targeting to a neovascular site.

Preferably, the targeting agent of the present invention is a drug delivery agent targeting to a neovascular site.

Preferably, the gelatin-like protein is gelatin, collagen, fibronectin, pronectin, vitronectin, or a combination thereof.

Preferably, the gelatin-like protein is a recombinant gelatin having an amino acid sequence derived from a partial amino acid of collagen.

Preferably, the recombinant gelatin comprises repeats of a sequence represented by Gly-X-Y characteristic to collagen and has a molecular weight of 2 KDa to 100 KDa. wherein X and Y each independently represent an amino acid and a plurality of Gly-X-Y sequences may be the same or different.

Preferably, the recombinant gelatin comprises repeats of a sequence represented by Gly-X-Y characteristic to collagen and has a molecular weight of 10 KDa to 90 KDa. wherein X and Y each independently represent an amino acid and a plurality of Gly-X-Y sequences may be the same or different.

Preferably, the recombinant gelatin comprises repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different.

Preferably, the cell adhesion signal sequence is an amino acid sequence represented by Arg-Gly-Asp.

Preferably, the amino acid sequence of the recombinant gelatin does not comprise any of serine and threonine.

Preferably, the amino acid sequence of the recombinant gelatin does not comprise any of serine, threonine, asparagine, tyrosine, and cysteine.

Preferably, the amino acid sequence of the recombinant gelatin does not comprise an amino acid sequence represented by Asp-Arg-Gly-Asp (SEQ ID NO: 2).

Preferably, the recombinant gelatin is represented by the following formula:

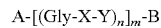

A-[(Gly-X-Y)$_n$]$_m$-B wherein A represents any amino acid or amino acid sequence, B represents any amino acid or amino acid sequence, there exist n amino acids each independently represented by X, there exist n amino acids each independently represented by Y, n represents an integer from 3 to 100, m represents an integer of 2 to 10, and n Gly-X-Y sequences may be the same or different.

Preferably, the recombinant gelatin is represented by the following formula:

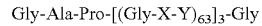

Gly-Ala-Pro-[(Gly-X-Y)$_{63}$]$_3$-Gly wherein there exist 63 amino acids each independently represented by X, there exist 63 amino acids each independently represented by Y, and n Gly-X-Y sequences may be the same or different.

Preferably, the recombinant gelatin has the following (1) or (2):

(1) the amino acid sequence shown in SEQ ID NO: 1; or
(2) an amino acid sequence having 80% or more homology to the amino acid sequence shown in SEQ ID NO: 1 and having an action to accumulate in newly formed blood vessels.

Preferably, the recombinant gelatin is crosslinked.

Preferably, the crosslinking is carried out using an aldehyde, condensing agent, or enzyme.

Preferably, the targeting agent of the present invention further comprises a labeled probe or a drug.

Preferably, the labeled probe is a fluorescent dye, a radioisotope, a nuclide used for PET, a nuclide used for SPECT, an MRI contrast medium, a CT contrast medium, or a magnetic material.

Preferably, the fluorescent dye is a quantum dot, indocyanine green, or a near-infrared fluorescent dye; each of the radioisotope, the nuclide used for PET, and the nuclide used for SPECT (Single photon emission computed tomography) is $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, or a complex thereof, or a combination thereof; and each of the MRI contrast medium, the CT contrast medium, and the magnetic material is gadolinium, Gd-DTPA, Gd-DTPA-BMA, Gd-HP-DO3A, iodine, iron, iron oxide, chromium, manganese, a complex or chelate complex thereof, or a combination thereof.

Preferably, the gelatin-like protein is physically or chemically bound to the labeled probe, directly or via a linker.

Preferably, the bond is a coordinate bond, a covalent bond, a hydrogen bond, hydrophobic interaction, or physical adsorption.

The present invention also provides a method for targeting a substance to a neovascular site, which comprises administering a gelatin-like protein to a subject. Preferably, there is provided a method for imaging a neovascular site, which comprises administering a gelatin-like protein to a subject. Preferably, there is provided a method for delivering a drug to a neovascular site as a target, which comprises administering a gelatin-like protein to a subject.

The present invention further provides use of a gelatin-like protein for production of a targeting agent to a neovascular site. Preferably, there is provided use of a gelatin-like protein for production of an imaging agent targeting to a neovascular site. Preferably, there is provided use of a gelatin-like protein for production of a drug delivery agent targeting to a neovascular site.

Advantageous Effects of Invention

The targeting agent to a neovascular site of the present invention enables the drug delivery to a neovascular site and the imaging of such a neovascular site, utilizing the effect of the agent to accumulate in the neovascular site. Moreover, the targeting agent to a neovascular site of the present invention is characterized in that it has a blood retention property higher than that of a commonly studied circular RGD compound and in that its stay in a neovascular site is short.

EMBODIMENTS FOR CARRYING OUT THE INVENTION

Figure 1:
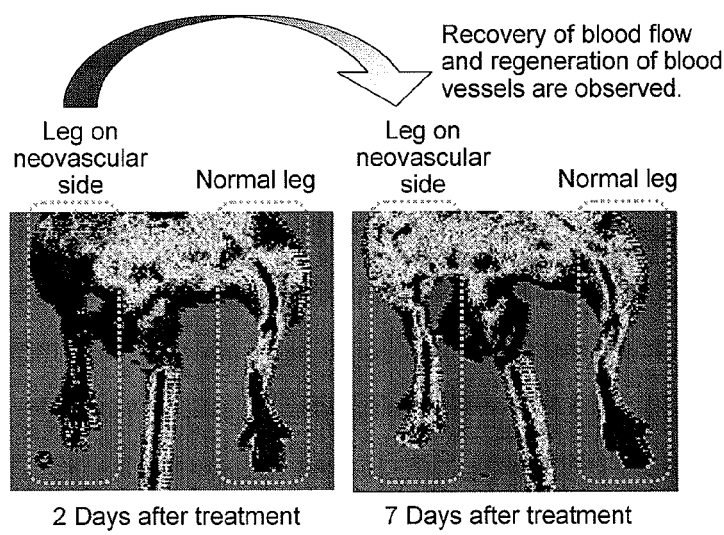
FIG. 1 shows evaluation of a "leg ischemia→neovascularization" model using a laser Doppler blood-flowmeter.

Embodiments for carrying out the present invention are described in detail below.

The type of the gelatin-like protein used in the present invention is not particularly limited, as long as it exhibits the effects of the present invention. The gelatin-like protein of the present invention is preferably any one of gelatin, collagen, fibronectin, pronectin and vitronectin, or a combination thereof. The origin of the gelatin-like protein is not particularly limited. The gelatin-like protein is preferably gelatin, and particularly preferably a recombinant gelatin.

As a recombinant gelatin that can be used in the present invention, a recombinant gelatin having an amino acid sequence derived from a partial amino acid sequence of collagen can be used. Examples of a recombinant gelatin that can be used include, but are not limited to, recombinant gelatins described in EP1014176A2, U.S. Pat. No. 6,992,172, WO2004-85473, and WO2008/103041. A recombinant gelatin preferably used as the recombinant gelatin of the present invention is described below.

The recombinant gelatin used in the present invention has original properties of naturally occurring gelatin and thus it is highly biocompatible. In addition, the recombinant gelatin is not directly obtained from natural sources and thus has no risk of causing BSE or the like. In this regard, it has an excellent property of being non-infectious. In addition, the recombinant gelatin used in the present invention is more homogenous than naturally occurring gelatin. Further, the recombinant gelatin has a predetermined sequence. Thus, it is possible to precisely design the recombinant gelatin in terms of strength and degradability with few errors by crosslinking or the like described below.

The molecular weight of the recombinant gelatin used in the present invention is preferably 2 KDa to 100 KDa, more preferably 2.5 KDa to 95 KDa, further preferably 5 KDa to 90 KDa, and most preferably 10 KDa to 90 KDa.

Preferably, the recombinant gelatin used in the present invention contains repeats of a sequence represented by Gly-X-Y characteristic to collagen. Here, a plurality of sequences each represented by Gly-X-Y may be the same or different. Gly in Gly-X-Y represents glycine. X and Y in Gly-X-Y represent any amino acids (and preferably any amino acids other than glycine). When gelatin/collagen is compared with other proteins in terms of the amino acid composition or sequence, the GXY sequence is characteristic to collagen and forms a highly specific partial structure. Glycine accounts for approximately one-third of the partial structure as a whole. Glycine is repeatedly found in the amino acid sequence at a rate of 1 out of every 3 amino acids. Glycine is the simplest amino acid. There are few restrictions to arrangement of the molecular chain of glycine and thus glycine highly contributes to regeneration of the helix structure upon gelatinization. Preferably, an amino acid represented by X or Y is rich in imino acid (proline or oxyproline) and the imino acid accounts for 10% to 45% of the amino acid sequence as a whole. Amino acids forming the GXY repeat structure account for preferably 80% or more, more preferably 95% or more, and most preferably 99% or more of the amino acid sequence as a whole.

A generally available gelatin contains charged polar amino acids and uncharged polar amino acids at a ratio of 1:1. Here, the term "polar amino acid" specifically refers to cysteine, aspartic acid, glutamic acid, histidine, lysine, asparagine, glutamine, serine, threonine, tyrosine, or arginine. In particular, the term "uncharged polar amino acid" refers to cysteine, asparagine, glutamine, serine, threonine, or tyrosine. The percentage of polar amino acids relative to all amino acids constituting the recombinant gelatin used in the present invention is 10% to 40% and preferably 20% to 30%. In addition, the percentage of uncharged polar amino acids relative to the polar amino acids is preferably 5% to less than 20% and more preferably less than 10%. Further, the amino acid sequence does not contain one amino acid and preferably two amino acids or more selected from among serine, threonine, asparagine, tyrosine, and cysteine.

In general, it is known that a polypeptide contains a minimal amino acid sequence that functions as a cell adhesion signal sequence (e.g., "Pathophysiology" (*Byotai Seiri*) Vol. 9, No. 7 (1990), p. 527, Nagai Shoten Co., Ltd.). It is preferable for a single molecule of the recombinant gelatin used in the present invention to have at least two cell adhesion signal sequences. Specifically, amino acids are shown by one-letter notation in a cell adhesion signal sequence. In view of an increase in types of adhering cells, examples of such sequence are: preferably an RGD sequence, an LDV sequence, an REDV (SEQ ID NO: 3) sequence, a YIGSR (SEQ ID NO: 4) sequence, a PDSGR (SEQ ID NO: 5) sequence, an RYVVLPR (SEQ ID NO: 6) sequence, an LGTIPG (SEQ ID NO: 7) sequence, an RNIAEIIKDI (SEQ ID NO: 8) sequence, an IKVAV (SEQ ID NO: 9) sequence, an LRE sequence, a DGEA (SEQ ID NO: 10) sequence, and an HAV sequence, more preferably an RGD sequence, a YIGSR (SEQ ID NO: 4) sequence, a PDSGR (SEQ ID NO: 5) sequence, an LGTIPG (SEQ ID NO: 7) sequence, an IKVAV (SEQ ID NO: 9) sequence, and an HAV sequence; and particularly preferably an RGD sequence. Among the RGD sequence, an ERGD (SEQ ID NO: 11) sequence is preferred.

In terms of arrangement of RGD sequences in the recombinant gelatin used in the present invention, the number of amino acids present between two RGD sequences is preferably 0 to 100 and more preferably 25 to 60. Preferably, the number of amino acids is not uniformly determined.

In view of cell adhesion/growth, the number of such minimal amino acid sequences in a single protein molecule is preferably 3 to 50, more preferably 4 to 30, particularly preferably 5 to 20, and most preferably 12.

The percentage of RGD motifs in the recombinant gelatin used in the present invention related to the total number of amino acids is preferably at least 0.4%. If the recombinant gelatin comprises 350 amino acids or more, each stretch of 350 amino acids contains preferably at least one RGD motif. The percentage of RGD motifs related to the total number of amino acids is more preferably at least 0.6%, further preferably at least 0.8%, still further preferably at least 1.0%, even further preferably at least 1.2%, and most preferably at least 1.5%. The number of RGD motifs in the recombinant gelatin is preferably at least 4, more preferably 6, further preferably 8, and even further preferably 12 to 16 per 250 amino acids. A percentage of RGD motifs of 0.4% corresponds to at least one RGD sequence per 250 amino acids. The number of RGD motifs is represented by an integer. Therefore, in order to achieve a percentage of RGD motifs of 0.4%, it is necessary for a gelatin comprising 251 amino acids to contain at least two RGD sequences. Preferably, the recombinant gelatin of the present invention contains at least 2 RGD sequences per 250 amino acids, more preferably at least 3 RGD sequences per 250 amino acids, and further preferably at least 4 RGD sequences per 250 amino acids. In another embodiment, the recombinant gelatin of the present invention comprises at least 4, preferably 6, more preferably 8, and further preferably 12 to 16 RGD motifs.

In addition, the recombinant gelatin may be partially hydrolyzed.

Preferably, the recombinant gelatin used the present invention has a structure comprising repeats of A-[(Gly-X-Y)n]m-B. Here, "m" is an integer of preferably 2 to 10 and more preferably 3 to 5. In addition, "n" is an integer of preferably 3 to 100, more preferably 15 to 70, and most preferably 50 to 65.

Preferably, a plurality of naturally occurring collagen sequence units are bound to form a repeat unit. The term "naturally occurring collagen" used herein may refer to any naturally occurring collagen. However, preferable examples thereof include type-I, type-II, type-III, type-IV, and type-V collagens. More preferably, type-I, type-II, and type-III collagens are used. In another embodiment, the origin of such collagen is preferably a human, bovine, pig, mouse, or rat and it is more preferably a human.

The isoelectric point of the recombinant gelatin used in the present invention is preferably 5 to 10, more preferably 6 to 10, and further preferably 7 to 9.5.

Preferably, the recombinant gelatin is not deaminated.

Preferably, the recombinant gelatin is not procollagen or does not comprise procollagen.

Preferably, the recombinant gelatin does not comprise telopeptide.

Preferably, the recombinant gelatin is a substantially pure collagen material prepared from a nucleic acid encoding a naturally occurring collagen.

Particularly preferably, the recombinant gelatin used in the present invention is a recombinant gelatin having the following (1) or (2):
(1) the amino acid sequence shown in SEQ ID NO: 1; or
(2) an amino acid sequence having 80% or more, more preferably 90% or more, and most preferably 95% or more homology to the amino acid sequence shown in SEQ ID NO: 1, and having an action to accumulate in newly formed blood vessels.

The recombinant gelatin used in the present invention can be produced by a gene recombination technique known to persons skilled in the art. For instance, it can be produced according to the method described in EP1014176A2, U.S. Pat. No. 6,992,172, WO2004/85473, or WO2008/103041. Specifically, a transformant is produced by obtaining a gene encoding the amino acid sequence of a predetermined recombinant gelatin, incorporating the gene into an expression vector to prepare a recombinant expression vector, and introducing the vector into an appropriate host. The obtained transformant is cultured in an appropriate medium to produce a recombinant gelatin. Therefore, the recombinant gelatin used in the present invention can be prepared by collecting the produced recombinant gelatin from the culture product.

If the obtained recombinant gelatin alone has insufficient properties, it may be mixed with other material, or a complex of recombinant gelatin and other material may be prepared. For example, it can be mixed with a different type of recombinant gelatin or a different biopolymer or synthetic polymer. Examples of a biopolymer include a polysaccharide, a polypeptide, a protein, a nucleic acid, and an antibody. Preferably, a polysaccharide, a polypeptide, or a protein is used. Examples of a polysaccharide, a polypeptide and a protein include collagen, gelatin, albumin, fibroin, and casein. Further, the above biopolymers may be partially chemically modified according to need. For instance, hyaluronic acid ethyl ester can be used. Examples of a polysaccharide include glycosaminoglycan represented by hyaluronic acid or heparin, chitin, and chitosan. Further, examples of a polyamino acid include poly-γ-glutamic acid.

The recombinant gelatin of the present invention can be chemically modified depending on the application thereof. Chemical modification may be performed via introduction of a low molecular compound or a different polymer (e.g., a biopolymer (sugar or protein), a synthetic polymer, or polyamide) into a carboxyl group or an amino group of a side chain of the recombinant gelatin or crosslinking between recombinant gelatin chains. For example, a carbodiimide-based condensing agent is used for introduction of a low molecular compound into the recombinant gelatin.

The crosslinking agent used in the present invention is not particularly limited, as long as the present invention can be carried out. It may be a chemical crosslinking agent or an enzyme. Examples of a chemical crosslinking agent include formaldehyde, glutaraldehyde, carbodiimide, and cyanamide. Preferably, formaldehyde or glutaraldehyde is used. Further, crosslinking of a recombinant gelatin can be conducted by light irradiation to a gelatin into which a photoreactive group has been introduced, light irradiation under the presence of a photosensitizer, or the like. Examples of a photoreactive group include a cinnamyl group, a coumarin group, a dithiocarbamyl group, xanthene dye, and camphorquinone.

In a case in which enzymatic crosslinking is carried out, an enzyme used is not particularly limited, as long as it has an action of causing crosslinking between recombinant gelatin chains. However, crosslinking can be carried out using preferably transglutaminase or laccase and most preferably transglutaminase. Examples of proteins that are enzymatically crosslinked by transglutaminase include, but are not particularly limited to, proteins having lysine residues and glutamine residues. A mammalian-derived or microorganism-derived transglutaminase may be used. Specific examples thereof include: the Activa series (produced by Ajinomoto Co., Inc.); commercially available mammalian-derived transglutaminases serving as reagents such as guinea pig liver-derived transglutaminase, goat-derived transglutaminase, and rabbit-derived transglutaminase (produced by Oriental Yeast Co., Ltd., Upstate USA Inc., Biodesign International, etc.); and a human-derived blood coagulation factor (Factor XIIIa, Haematologic Technologies, Inc.).

Crosslinking of the recombinant gelatin comprises the following two steps: a step of mixing a recombinant gelatin solution and a crosslinking agent; and a step of causing a reaction in the obtained homogenous solution.

According to the present invention, the mixing temperature for treating the recombinant gelatin with a crosslinking agent is not particularly limited, as long as the solution can be homogenously agitated. However, it is preferably 0° C. to 40° C., more preferably 0° C. to 30° C., further preferably 3° C. to 25° C., still further preferably 3° C. to 15° C., even further preferably 3° C. to 10° C., and particularly preferably 3° C. to 7° C.

After agitation of the recombinant gelatin and the crosslinking agent, the temperature can be increased. The reaction temperature is not particularly limited, as long as crosslinking can proceed. However, in view of denaturation or degradation of the recombinant gelatin, it is substantially 0° C. to 60° C., preferably 0° C. to 40° C., more preferably 3° C. to 25° C., further preferably 3° C. to 15° C., still further preferably 3° C. to 10° C., and particularly preferably 3° C. to 7° C.

According to the present invention, the above-described gelatin-like protein (particularly preferably, a recombinant gelatin having an amino acid sequence derived from a partial amino acid sequence of collagen) is administered to a subject (e.g. a mammal such as a human), so that a substance can be targeted to a neovascular site. That is to say, according to the present invention, since a gelatin-like protein targets to a neovascular site and accumulates therein, a desired substance can be delivered to the neovascular site as a target. Accordingly, the targeting agent to a neovascular site of the present invention can be used as an imaging agent targeting to a neovascular site, for example, and it can also be used as a drug delivery agent targeting to a neovascular site.

When the targeting agent to a neovascular site of the present invention is used as an imaging agent targeting to a neovascular site, the targeting agent can comprise a labeled probe as well as a gelatin-like protein. In addition, the targeting agent to a neovascular site of the present invention is used as a drug delivery agent targeting to a neovascular site, the targeting agent can comprise a drug (a therapeutically effective ingredient) as well as a gelatin-like protein. Moreover, if necessary, the targeting agent can comprise both a labeled probe and a drug (a therapeutically effective ingredient), together with a gelatin-like protein.

Examples of a labeled probe used when the targeting agent of the present invention is used as an imaging agent include a fluorescent dye, a radioisotope, a nuclide used for PET, a nuclide used for SPECT, an MRI contrast medium, a CT contrast medium, and a magnetic material. Preferred examples of the radioisotope, the nuclide used for PET, and the nuclide used for SPECT (single photon emission computed tomography) include $^{11}C$, $^{13}N$, $^{15}O$, $^{18}F$, $^{66}Ga$, $^{67}Ga$, $^{68}Ga$, $^{60}Cu$, $^{61}Cu$, $^{62}Cu$, $^{67}Cu$, $^{64}Cu$, $^{48}V$, Tc-99m, $^{241}Am$, $^{55}Co$, $^{57}Co$, $^{153}Gd$, $^{111}In$, $^{133}Ba$, $^{82}Rb$, $^{139}Ce$, Te-123m, $^{137}Cs$, $^{86}Y$, $^{90}Y$, $^{185/187}Re$, $^{186/188}Re$, $^{125}I$, a complex thereof, and a combination thereof. Examples of the MRI contrast medium, the CT contrast medium, and the magnetic material include gadolinium, Gd-DTPA, Gd-DTPA-BMA, Gd-HP-DO3A, iodine, iron, iron oxide, chromium, manganese, and a complex or chelate complex thereof. Moreover, examples of the fluorescent dye include a known quantum dot, indocyanine green, and a near-infrared fluorescent dye (Cy5.5, Cy7, AlexaFluoro, etc.).

Preferably, the gelatin-like composition is physically or chemically bound to the labeled probe, directly or via a linker. Specifically, the bond is preferably a coordinate bond, a covalent bond, a hydrogen bond, hydrophobic interaction, or physical adsorption. In all cases, a bond, a linker and a binding method, which have been known, can be adopted.

When the targeting agent of the present invention is used as a drug delivery agent, it is possible to encapsulate a drug (a therapeutically effective ingredient) as well as the gelatin-like protein into the targeting agent of the present invention. The drug is a physiologically active ingredient. Specific examples thereof include percutaneous absorbents, topical therapeutic agents, oral therapeutic agents, cosmetic ingredients, and supplement ingredients. Specific examples of the drug include anti-inflammatory agents, antibacterial agents, antibiotics, immunosuppressive agents, antioxidants, anticancer agents, vitamins, nucleic acids, and antibodies. Particularly preferred examples thereof are anti-inflammatory agents. Both steroidal and nonsteroidal anti-inflammatory agents may be used. Examples of anti-inflammatory agents include aspirin, acetaminophen, phenacetin, indomethacin, diclofenac sodium, piroxicam, fenoprofen calcium, ibuprofen, chlorpheniramine maleate, diflunisal, dexamethasone sodium phosphate, paclitaxel, docetaxel, 5-fluorouracil, Topotecin, cisplatin, rapamycin, tacrolimus, and cyclosporin. Vitamins that can be used are both water- and fat-soluble vitamins. Examples of such vitamins include vitamin A, the vitamin B group, vitamin C, the vitamin D group, vitamin E, and vitamin K. Specific examples of drugs are described above. However, examples of the drugs that can be used in the present invention are not limited to the above drugs.

The targeting agent (imaging agent, drug delivery agent, etc.) of the present invention can be used for the diagnosis of disease, the diagnosis of therapeutic effects, the analysis of pathological conditions, or treatment; the diagnosis of disease associated with angiogenesis and/or the analysis of pathological conditions, and the treatment thereof; or a therapeutic method involving angiogenesis, a method for enhancing therapeutic effects, which involves angiogenesis, and determination of such therapeutic effects.

Examples of target diseases and/or target treatment methods in the present invention include: malignant tumors; ischemic diseases; angiogenesis therapy, cell/tissue regenerative therapy, or cell implantation therapy; diabetic gangrene; ulcer; hearing loss; heart diseases; arteriosclerosis; acute coronary syndromes; acute myocardial infarction; unstable angina pectoris; and cardiac sudden death. Diagnostic methods that can be applied in the present invention include PET, SPECT, CT, MRI, endoscopy, and use of a fluorescence detector.

The dose, the usage, and the dosage form of the targeting agent of the present invention can be appropriately determined depending of the purpose of use. For example, the targeting agent of the present invention can be directly administered in vivo to a desired site. Alternatively, it may be suspended in a liquid excipient such as an aqueous solvent (e.g., distilled water for injection, physiological saline for injection, or buffer (e.g., phosphate or citrate buffer) (pH 5 to 8)) so as to be administered via injection, external application, or the like. In addition, it may be mixed with an adequate excipient in the form of ointment, gel, cream, or the like so as to be externally applied. That is, the administration route of the targeting agent of the present invention may be the oral route or the parenteral route (e.g., intravenous administration, intramuscular administration, subcutaneous administration, or intradermal administration). Examples of the dosage form include: oral administration agents such as tablets, powders, capsules, granules, extracts, and syrups; and parenteral administration agents such as injections (e.g., intravenous injections, muscular injections, subcutaneous injections, and intradermal injections).

A formulation of the targeting agent of the present invention can be prepared by a method known to persons skilled in the art. For example, if liquid is used as a carrier for a formulation, the targeting agent of the present invention can be dissolved or dispersed in the liquid. Alternatively, if a powder is used as a carrier for a formulation, the targeting agent of the present invention can be mixed with or adhere to the powder. Further, if necessary, a pharmaceutically acceptable additive (e.g., a preservative, a stabilizer, an antioxidant, an excipient, a binder, a disintegrator, a wetting agent, a lubricant, a coloring agent, an aromatic agent, a corrigent, a coating, a suspending agent, an emulsifier, a dissolution adjuvant, a buffer, a tonicity agent, a plasticizer, a surfactant, or a soothing agent) can be mixed therewith.

The applied dose of the recombinant gelatin is not particularly limited. However, for example, it can be 10 µg/kg to 100 mg/kg, and preferably 100 µg/kg to 10 mg/kg per kg of body weight of a subject organism, to which it is to be administered.

The present invention is hereafter described in greater detail with reference to the following examples, although the present invention is not limited thereto.

EXAMPLES

As a recombinant gelatin, CBE3 (WO2008-103041) described below was prepared.
CBE3
Molecular weight: 51.6 kD
Structure: GAP[(GXY)63]3G
Number of amino acids: 571
Number of RGD sequences: 12
Imino acid content: 33%
(Substantially 100% of amino acids form the GXY repeat structure. The amino acid sequence of CBE3 does not contain any of serine, threonine, asparagine, tyrosine, and cysteine. CBE3 has the ERGD sequence.)
Isoelectric point: 9.34
Amino acid sequence (SEQ ID NO: 1 in the Sequence Listing) (This amino acid sequence corresponds to the amino acid sequence shown in SEQ ID NO: 3 in WO2008/103041. Note that "X" at the end was modified to "P.")

```
GAP(GAPGLQGAPGLQGMPGERGAAGLPGPKGERGDAGPKGADGAPG
APGLQGMPGERGAAGLPGPKGERGDAGPKGADGAPGKDGVRGLAGPI
GPPGERGAAGLPGPKGERGDAGPKGADGAPGKDGVRGLAGPIGPPGP
AGAPGAPGLQGMPGERGAAGLPGPKGERGDAGPKGADGAPGKDGVR
GLAGPP)3G
```

In the Examples described below, CBE3 above used as a recombinant gelatin is described as "R-Gel" unless specified otherwise.

(1) Production of Leg Ischemia→Neovascularization Model (Animal Model)

An animal model, in the ischemic site of which a newly formed blood vessel regenerated as a result of self-healing, namely, and a regenerated newly formed blood vessel was to be formed, was produced.

10% Nembutal (diluted with a normal saline) was intraperitoneally administered to a C57BL6 mouse (male, 6-week-old; manufactured by Japan SLC, Inc.) at a weight of 1/10 of the body weight thereof, and the mouse was then treated under anesthesia. Hair was cut out of left and right legs, and thereafter, the removal of blood vessels, cauterization and hemostasis were performed on only the right leg.

A cauterization knife (Tagawa Denki Kenkyusho Company) was used for the removal of blood vessels. While performing ablation from the muscle, the hemostasis of blood vessels, and the removal of the blood vessels, a majority of the femoral artery was removed. After confirming the hemostasis of the treated site, the treated site was washed with a normal saline, and the treated site was sutured With regard to the thus produced leg ischemia model, the blood flow conditions of a treated leg (right leg) and an untreated leg (left leg) were measured using a laser Doppler blood-flowmeter, so as to confirm whether the treatment of leg ischemia had been successfully carried out, or whether the subsequent angiogenesis (blood flow recovery) had progressed.

As a laser Doppler blood-flowmeter, Moor LDI (Moor) was used, and upon the measurement, the mouse was anesthetized with Nembutal, and at the same time, the backside of each leg was incubated at 37° C. on an incubation plate, and then blood flow was measured. The measured blood flow data was analyzed using moor LDI Software Version 5.1. The blood flow condition of the treated leg (right leg) was compared with the untreated leg (left leg) that was a normal leg, so as to determine whether the leg ischemia treatment had been successfully carried out, or whether blood flow recovery (angiogenesis) had occurred.

Figure 2:
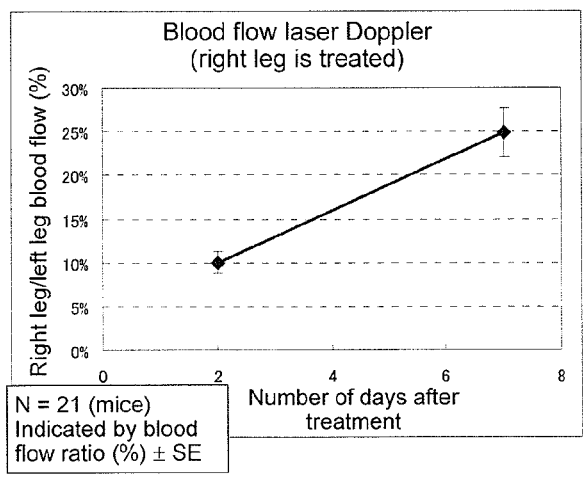
FIG. 2 shows the blood flow ratio between a treated leg and an untreated leg.

As a result of the aforementioned experiment on the mice (N=21), it was found that the blood flow recovery rate indicated by formula [1]: "mean value of blood flow of treated leg/mean value of blood flow of untreated leg×100" was approximately 10% on Day 2 after the treatment, and thus that the treatment of leg ischemia had been successfully carried out. On the other hand, on Day 7 after the treatment, it was found that the blood flow recovery rate indicated by the formula [1] progressed to be approximately 25%, and that regeneration of blood vessels occurred as a result of natural healing after leg ischemia, namely, regenerated newly formed blood vessels were formed (see FIG. 1 and FIG. 2). Thus, the animal 7 days after the treatment was used as a "leg ischemia→neovascularization" model animal in the subsequent experiments.

(2) iodine-labeling ($^{125}$I) of R-Gel

R-Gel was labeled with $^{125}$I according to a chloramine T method. 1 mg of R-Gel was dissolved in 1 mL of buffer A (0.5M phosphate buffer, 0.5M NaCl, pH 7.5). To 200 μL of the obtained solution, 5 μL of an NaI/NaOH solution was added, and 100 μL of 0.2 mg/mL chloramine T/buffer A was further added thereto (chloramine T; Nacalai Tesque, Inc.). The obtained solution was blended with the use of Vortex for 2 minutes. Thereafter, 100 μL, of a 4 mg/mL SMS (sodium disulfite) aqueous solution was added to the reaction solution, and the obtained solution was then blended with the use of a Vortex for 2 minutes (mixed solution B).

Figure 3:
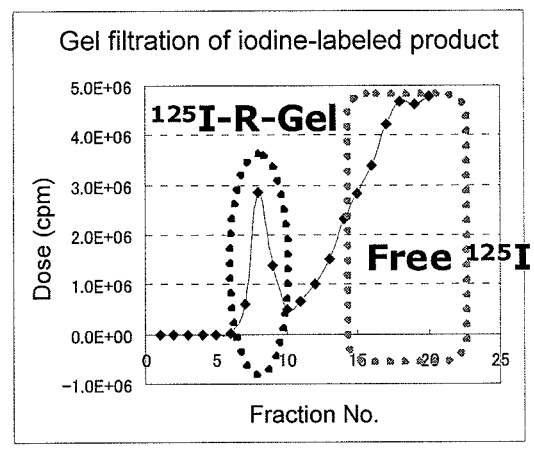
FIG. 3 shows the $^{125}$I labeling of R-Gel.

The mixed solution B was applied to a PD-10 column (GE Healthcare) that had previously been equilibrated with PBS (phosphate buffer), and elution was then carried out with PBS. 500 μL each of the eluant was recovered as a fraction. The amount of γ-ray radiation of each recovered fraction was measured using Auto Well Gamma System (ARC-380: Aloka) so as to measure $^{125}$I in the fraction, and the $^{125}$I-labeled R-Gel was then separated from free $^{125}$I (FIG. 3).

Thereby, the $^{125}$I-labeled R-Gel was obtained (hereinafter referred to as "$^{125}$I-R-Gel."). For quantification of a protein, a BCA method was applied (BCA Protein Assay Reagent: PIERCE). The $^{125}$I-labeled R-Gel was obtained in the form of a 0.1 mg/mL $^{125}$I-R-Gel/PBS solution with 1,500,000 cpm/mL.

(3) Body Distribution of R-Gel that Involves Use of $^{125}$I-R-Gel

200 μL of the $^{125}$I-R-Gel produced in (2) above was administered into the caudal vein of a DDY mouse (male, 6-week-old; Japan SLC, Inc.), and the distribution of the $^{125}$I-R-Gel in tissues was determined by measuring the amount of γ-ray radiation in individual organs and tissues and the amount of γ-ray radiation in the discharged urine using Auto Well Gamma System (ARC-380: Aloka), 1 hour, 3 hours, 6 hours and 24 hours after the administration. The amount of γ-ray radiation in individual organs and tissues was directly measured by dissecting the mouse, and the amount of γ-ray radiation in the blood was determined by calculating it based on the amount of γ-ray radiation in 200 μL of the blood collected from the heart.

Upon administration of the $^{125}$I-R-Gel, the administered $^{125}$I-R-Gel amount/the amount of γ-ray radiation was defined as an amount obtained by subtracting 'the amount of γ-ray radiation remaining in the syringe after administration of the $^{125}$I-R-Gel into the caudal vein' from 'the amount of γ-ray radiation in a state in which the $^{125}$I-R-Gel is placed in the syringe." It is to be noted that calculation was carried out based on the precondition that total blood volume is 8% by weight of the body weight. The amount of $^{125}$I-R-Gel accumulating in the thyroid gland was 1% or less of the administered amount, almost no free $^{125}$I was present, and the binding of $^{125}$I with R-Gel was not lost.

The value obtained by adding the amounts of γ-ray radiation in all of the organs and tissues, except for the amount of γ-ray radiation in the discharged urine, was defined as 'the amount of $^{125}$I-R-Gel remaining in the body,' and the value obtained by dividing the thus obtained value by the amount of γ-ray radiation administered was defined as 'the percentage of $^{125}$I-R-Gel remaining in the body.'

Figure 4:
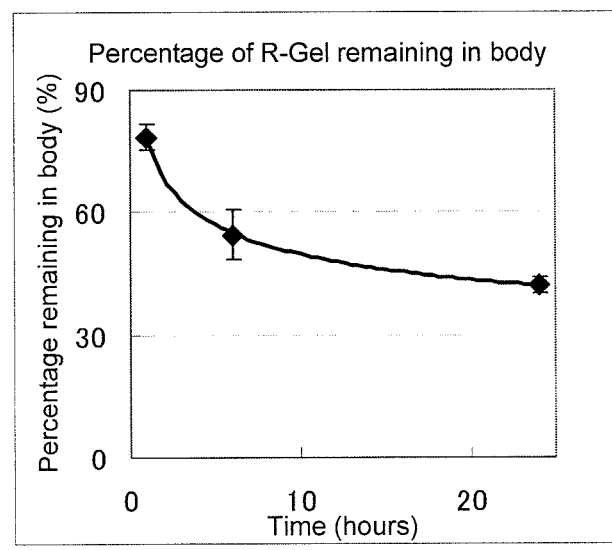
FIG. 4 shows the percentage of R-Gel remaining in the body.

As a result, it was found that 40% or more of $^{125}$I-R-Gel remained in the living body even 24 hours after the administration (FIG. 4). In "Evaluation of a radiolabelled cyclic DTPA-RGD analogue for tumor imaging and radionuclide therapy. Int. Journal of Cancer 2000; 90:186-198," P M Van Hagen et al. describe that 85% or more of circular RGD peptide (cyclic-RGDyK) is recovered by being discharged to the urine 24 hours after the administration, namely, that the amount of the circular RGD peptide remaining in the body is 15% or less. From the descriptions of this publication, it was found that R-Gel has high retention property in the body.

Figure 5:
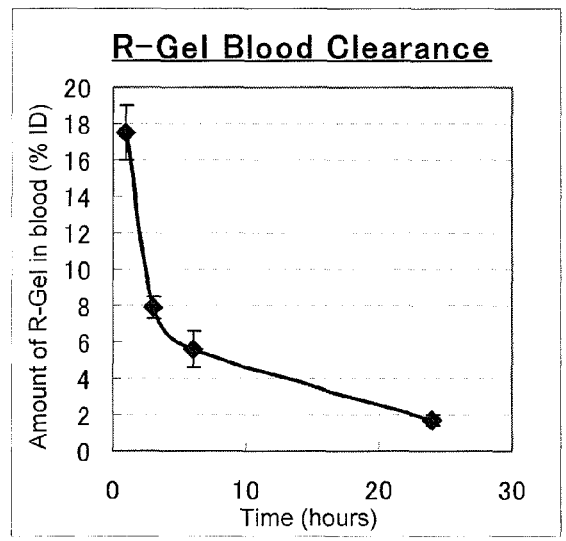
FIG. 5 shows the blood clearance of R-Gel.

Moreover, $^{125}$I-R-Gel blood clearance was measured based on the blood level of $^{125}$I-R-Gel indicated by % ID (percentage of the Injected Dose). As a result, the blood level (% ID) in a predetermined time after administration was 17.5±1.5% (1 hour), 7.9±0.6% (3 hours), 5.6±1.0% (6 hours), and 1.7±0.3% (24 hours) (indicated by Average±S.D.) (FIG. 5). An RGD peptide, a circular RGD peptide and an analog thereof are rapidly discharged from the body, and thus, they show rapid blood clearance. In contrast, R-Gel was found to show a high blood retention property. With regard to the blood clearance of circular RGD, for example, Wu Y, Zhang X, Xiong Z, et al. describe in "microPET imaging of glioma $\alpha_v\beta_3$-integrin expression using $^{64}$Cu-labeled tetrameric RGD eptide. J Nucl Med 2005; 46: 1707-18" that the blood level of $^{64}$Cu-DOTA-E{E[cyclic-(RGDfK)]$_2$}$_2$ as a tetrameric peptide construct of circular RGD (cylclic-RGDfK) is 0.61±0.01% (30 minutes after administration) and 0.21±0.01% (4 hours after administration), and thus, it is found that the blood clearance of the circular RGD is extremely rapid. From the above-described results, it is found that R-Gel has a "good blood retention property" useful as a drug delivery agent that is superior to that of a prior art.

(4) Accumulation of $^{125}$I-R-Gel in the Neovascular Site of the "Leg Ischemia→Neovascularization Model"

200 μL, of the $^{125}$I-R-Gel produced in (2) above was administered into the caudal vein of the "leg ischemia→neovascularization model" produced in (1) above, and the distribution of the $^{125}$I-R-Gel in tissues was determined by measuring the amount of γ-ray radiation in individual organs and tissues and the amount of γ-ray radiation in the discharged urine using the Auto Well Gamma System, 3 hours and 24 hours after the administration. The amount of γ-ray radiation in individual organs and tissues was directly measured by dissecting the mouse, and the amount of γ-ray radiation in the blood was determined by calculating it based on the amount of γ-ray radiation in 200 μL of the blood collected from the heart.

Upon administration of the $^{125}$I-R-Gel, the administered $^{125}$I-R-Gel amount/the amount of γ-ray radiation was defined as an amount obtained by subtracting 'the amount of γ-ray radiation remaining in the syringe after administration of the $^{125}$I-R-Gel into the caudal vein' from 'the amount of γ-ray radiation in a state in which the $^{125}$I-R-Gel is placed in the syringe." It is to be noted that calculation was carried out based on the precondition that total blood volume is 8% by weight of the body weight. The amount of $^{125}$I-R-Gel accumulating in the thyroid gland was 1% or less of the administered amount, almost no free $^{125}$I was present, and the binding of $^{125}$I with R-Gel was not lost.

Moreover, by measuring blood flow recovery level in individual mice using a laser Doppler blood-flowmeter, comparisons were made in terms of the blood flow recovery level and the $^{125}$I-R-Gel accumulation level in the "neovascular site."

Furthermore, for comparison examination, beef bone-derived alkali-treated gelatin (hereinafter referred to as an "animal gelatin") in the same weight concentration as that of R-Gel was treated in the same manner as that described in (2) above, so as to prepare $^{125}$I-animal gelatin. This $^{125}$I-animal gelatin was administered to the "leg ischemia→neovascularization model" as in the case of $^{125}$I-R-Gel, and the body distribution thereof was then measured in the same manner as that for $^{125}$I-R-Gel.

When the term "leg" is used with regard to the "leg ischemia→neovascularization model," it mainly means a region corresponding to a portion of a leg ischemia model to be subjected to a femoral artery removal treatment, which includes a femoral portion ranging from the base of the leg to the toe. Accumulation of animal gelatin or R-Gel in the neovascular site was evaluated based on the ratio of the amount of the substance accumulating in the right leg (neovascular leg) to the amount of the substance accumulating in the left leg (normal leg) (hereinafter this value is referred to as "the percentage of the concerned substance accumulating in the neovascular site"), which is represented by the formula: "the amount of the substance in the right leg as a treated leg"/"the amount of the substance in the left leg as an untreated leg"×100.

In a state in which blood flow recovery was insufficient, both animal gelatin and R-Gel were observed to significantly highly accumulate in the right leg (neovascular leg) than in the left leg (normal leg). On the other hand, in a state in which such blood flow recovery progressed, namely, in a state in which angiogenesis progressed, the accumulation of animal gelatin in the right leg was at almost the same level as the accumulation thereof in the normal left leg, and thus, there was no significant difference. However, the accumulation of R-Gel in the right leg was significantly higher than the accumulation thereof in the normal left leg. More specifically, in the group of mice having a blood flow recovery of 15%, "the percentage of either animal gelatin or R-Gel accumulating in the neovascular site" was approximately 160%. In the group of mice having a blood flow recovery of 33%, "the percentage of R-Gel accumulating in the neovascular site" was 125%, and "the percentage of animal gelatin accumulating in the neovascular site" was 119%. Thus, both R-Gel and animal gelatin were observed to accumulate in the neovascular site. In the group of mice having a blood flow recovery of 50%, "the percentage of R-Gel accumulating in the neovascular site" was 125%, and "the percentage of animal gelatin accumulating in the neovascular site" was 97%.

From the above-described results, accumulation of animal gelatin and R-Gel in the neovascular site was confirmed.

(5) Production of bFGF-Induced Subcutaneous Neovascular Model

Gelatin gel containing a basic fibroblast growth factor (bFGF) was embedded into the subcutis of the dorsal portion of a mouse, so as to produce a subcutaneous neovascular model. As gelatin gel, MedGel pI5 (MedGel Corporation) was used. A sterilized aqueous solution containing 50 µg of bFGF was added to 2 mg of MedGel pI5, on which an EOG sterilization treatment had been performed, and the obtained mixture was then swollen at 4° C. overnight. The resultant was used as bFGF gel.

The thus produced bFGF gel was embedded into the subcutis of the dorsal portion of a C57BL6 mouse (male, 6-week-old; Japan SLC, Inc.). The embedded position was a position that was about 1.5 cm from the midline tail on the dorsal portion of the mouse. Thereby, one week after the embedding, it was confirmed that neovascularization was induced in the subcutis of the dorsal portion of the mouse. Hereafter, a model, in which neovascularization was induced in the subcutis approximately 1 week after the embedding of the bFGF gel, is referred to as a "bFGF-induced subcutaneous neovascular model." The experiment was carried out by the method described in "Y Tabata, Y Ikada. Vascularization effect of basic fibroblast growth factor released from gelatin hydrogels with different biodegradabilities. Biomaterials. 1999; 20: 2169-2175."

(6) Cy7 Labeling of R-Gel, Cyclo-RGDfK, PSK and Animal Gelatin

R-Gel, pig skin-derived gelatin (hereinafter referred to as PSK), animal gelatin and cyclo-RGDfK (AnaSpec, Inc.) were labeled with a fluorescent dye Cy7.

As Cy7, Cy7 mono-reactive NHS ester manufactured by GE Healthcare was used. The Cy7 NHS ester was dissolved in a concentration of 10 mg/mL in DMSO (dimethyl sulfoxide). 10 µL of Cy7 NHS ester/DMSO was mixed with an equimolar amount of R-Gel in a 0.1 M Sodium Carbonate buffer (pH 9.3), and the mixture was then reacted under light-shielded conditions at room temperature for 1 hour. At the same time, another product was also produced by reacting 10 µL of Cy7 NHS ester/DMSO with 1 mg of R-Gel under the same conditions as those described above. The obtained reaction product was applied to a PD-10 column that had previously been equilibrated with PBS (phosphate buffer), and elution was then carried out with a sufficient amount of PBS. While measuring the fluorescence level of the eluant, Cy7-labeled R-Gel (hereinafter referred to as Cy7-R-Gel) was separated from a Cy7-unreacted product, so as to obtain Cy7-R-Gel.

Likewise, 10 µL of Cy7 NHS ester/DMSO was mixed with an equimolar amount of PSK in a 0.1 M Sodium Carbonate buffer (pH 9.3), and the mixture was then reacted under light-shielded conditions at room temperature for 1 hour. At the same time, another product was also produced by reacting 10 µL of Cy7 NHS ester/DMSO with 1 mg of PSK under the same conditions as those described above. The obtained reaction product was applied to a PD-10 column that had previously been equilibrated with PBS (phosphate buffer), and elution was then carried out with a sufficient amount of PBS. While measuring the fluorescence level of the eluant, Cy7-labeled PSK (hereinafter referred to as Cy7-PSK) was separated from a Cy7-unreacted product, so as to obtain Cy7-PSK.

Likewise, 10 µL of Cy7 NHS ester/DMSO was mixed with an equimolar amount of animal gelatin in a 0.1 M Sodium Carbonate buffer (pH 9.3), and the mixture was then reacted under light-shielded conditions at room temperature for 1 hour. At the same time, another product was also produced by reacting 10 µL of Cy7 NHS ester/DMSO with 1 mg of PSK under the same conditions as those described above. The obtained reaction product was applied to a PD-10 column that had previously been equilibrated with PBS (phosphate buffer), and elution was then carried out with a sufficient amount of PBS. While measuring the fluorescence level of the eluant, Cy7-labeled animal gelatin (hereinafter referred to as Cy7-animal gelatin) was separated from a Cy7-unreacted product, so as to obtain Cy7-animal gelatin.

Likewise, 10 µL of Cy7 NHS ester/DMSO was mixed with an equimolar amount of cyclo-RGDfK in a 0.1 M Sodium Carbonate buffer (pH 9.3), and the mixture was then reacted under light-shielded conditions at room temperature for 1 hour. The obtained reaction product was applied to a PD-10 column that had previously been equilibrated with PBS (phosphate buffer), and elution was then carried out with a sufficient amount of PBS. While measuring the fluorescence level of the eluant, Cy7-labeled cyclo-RGDfK (hereinafter referred to as Cy7-cyclo-RGDfK) was separated from a Cy7-unreacted product, so as to obtain Cy7-cyclo-RGDfK.

(7) Neovascular Imaging in bFGF-Induced Subcutaneous Neovascular Model

Cy7-R-Gel, Cy7-PSK or Cy7-cyclo-RGDfK was administered to the bFGF-induced subcutaneous neovascular model produced in (5) above, and a fluorescence imaging experiment was then carried out from the outside of the body of a mouse. The dose was 200 μL, and as a administration route, administration was carried out via caudal vein.

For detection of a fluorescence signal, measurement, and imaging, Lumino image analyzer LAS5000 (a trial product of Fujifilm Corporation) was used. A visible light image and a fluorescence image were simultaneously taken, and the two images were then overlapped to identify a site from which fluorescence was emitted. In order to take such a fluorescence image, indicent light-IR light source was used as a light source, and a 785-nm band-pass filter was used as a filter. For image analysis and quantification of signal strength, software, MultiGauge (Fujifilm Corporation) was used.

Figure 6:
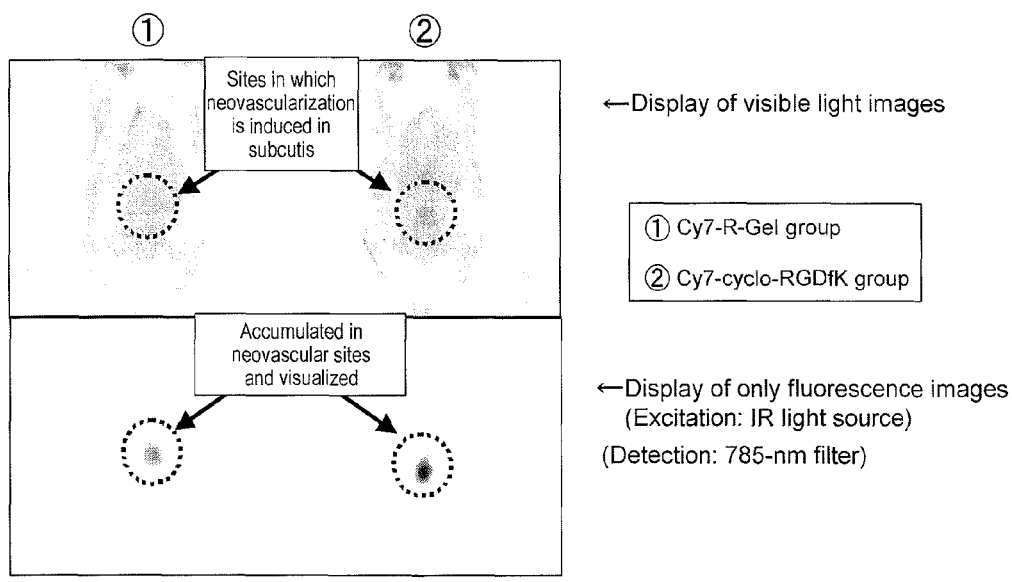
FIG. 6 shows the imaging of neovascular sites in bFGF-induced neovascular models.

As a result, using Cy7-R-Gel, Cy7-PSK and Cy7-cyclo-RGDfK, the inventors succeeded in imaging the neovascular site of a bFGF-induced subcutaneous neovascular model from the outside of the body (FIG. 6). (It is possible that the visible light image and the fluorescence image are displayed by overlapping them and each fluorescence intensity is color-coded. However, since black-and-white images were used in the present specification, the visible light image and the fluorescence image were displayed, separately.)

Figure 7:
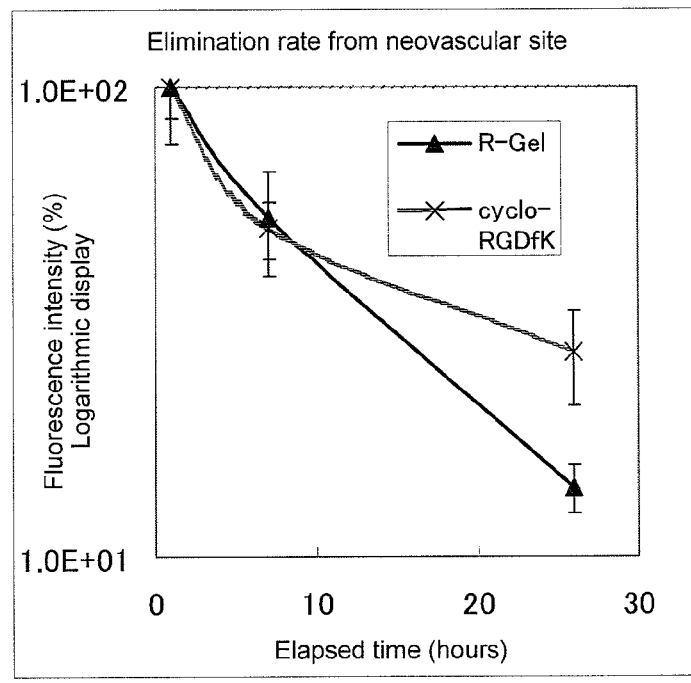
FIG. 7 shows an elimination rate from a neovascular site.

At the same time, fluorescence intensity in the neovascular site was measured over time, and a change in the fluorescence intensity was shown. The fluorescence intensity accumulated 1 hour after administration was set at 100, and a change in the value of the fluorescence intensity over time was shown (FIG. 7). As a result, it was found that Cy7-R-Gel disappeared from the neovascular site more rapidly than Cy7-cyclo-RGDfK did, and thus that the Cy7-R-Gel is suitable for application as an imaging agent, regarding which rapid signal disappearance from the neovascular site is required after signal detection.

(8) Inhibition of Accumulation of R-Gel in Neovascular Site by Previous Administration of Cyclo-RGDfK In order to evaluate whether accumulation of R-Gel in neovascular site is targeting caused by the same mechanism as that of circular RGD peptide cyclo-RGDfK, whether accumulation of R-Gel would be inhibited by previously administering a large amount of cyclo-RGDfK was examined. Unlabeled cyclo-RGDfK was dissolved in a concentration of 1 mg/ml in ultrapure water, and thereafter, 100 μL of the obtained solution was administered to a mouse via caudal vein administration. Thirty minutes later, 100 μL of Cy7-R-Gel was administered thereto via caudal vein administration. As a control, instead of cyclo-RGDfK, 100 μL of PBS (phosphate buffer) was administered to a mouse via caudal vein administration, and thirty minutes later, 100 μL of Cy7-R-Gel was administered thereto via caudal vein administration.

Figure 8:
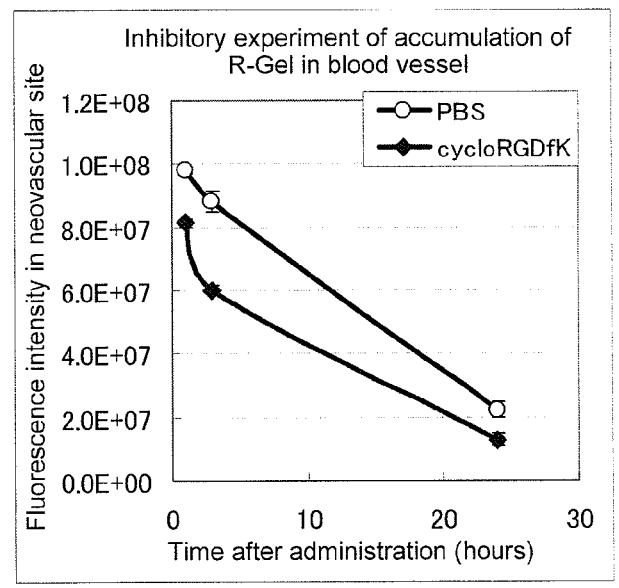
FIG. 8 shows inhibition of the accumulation of R-Gel in newly formed blood vessels by cyclo-PGDfK.

After completion of the administration, fluorescence intensity in the neovascular site was measured over time. When the fluorescence intensity was measured 1 hour after the administration, the fluorescence intensity in the PBS administration group was 98063583±1200251 (average±S.D.), whereas the fluorescence intensity in the cyclo-RGDfK administration group was 81431011±1373625 (average±S.D.). Thus, the fluorescence intensity in the cyclo-RGDfK administration group was significantly low. Likewise, in the measurement 3 hours after the administration, the fluorescence intensity in the PBS administration group was 88124139±3438695 (average±S.D.), whereas the fluorescence intensity in the cyclo-RGDfK administration group was 60269975±1267782 (average±S.D.). In the measurement 24 hours after the administration, the fluorescence intensity in the PBS administration group was 22196881±2549892 (average±S.D.), whereas the fluorescence intensity in the cyclo-RGDfK administration group was 12763810±1927458 (average±S.D.). Hence, in all of the cases, the fluorescence intensity in the cyclo-RGDfK administration group was significantly lower than the fluorescence intensity in the PBS administration group (t<0.05) (FIG. 8).

These results demonstrated that previous administration of a large amount of cyclo-RGDfK inhibits the effect of R-Gel to accumulate in blood vessels, and that the accumulation of R-Gel in blood vessels is caused by the same mechanism as that of cyclo-RGDfK or the like.

(9) Production of Cancer-Bearing Animal Model

Animal to be used: BALB/c mouse, female, 6-week-old
Cancer cells to be transplanted: Colon-26 (cells derived from BALB/c mouse colon cancer)
This is a homograft model.

As a tumor-bearing animal model, a cancer-bearing animal was produced. As an animal, BALB/c mouse (female, 6-week-old; Japan SLC, Inc.) was used. Tumor was produced using a cancer cell homograft model. As cancer cells, Colon-26 (which were cells derived from BALB/c mouse colon cancer) was used, and these cells were cultured in large scale in an RPMI1640 medium containing 10% fetal bovine serum. For the culture, a T-225 flask was used. Using EDTA-containing 0.25% trypsin, the growing cancer cells were removed from the bottom of the flask, and a culture supernatant was then removed by centrifugation. Thereafter, the solution was replaced with PBS (phosphate buffer), and the cell concentration was then counted using a cell counter. Finally, the culture was diluted so that the Colon-26 cells could be present in a concentration of $1\times10^6$ cells/mL in PBS.

Using a syringe, 100 μL of the obtained Colon-26 cell solution (=$1\times10^5$ cells) was transplanted into the BALB-c mouse (female, 6-week-old) by embedding it into the subcutis of the left leg thereof via subcutaneous administration. Approximately 12 days after completion of the transplantation, a tumor with a size of 100 mm$^3$ or less was formed. This mouse was used as a tumor animal or a cancer-bearing animal in the subsequent experiments. Hereinafter, this animal is referred to as a cancer-bearing animal.

(10) Imaging of Tumor Site and Tumoral Neovascular Site of Cancer-Bearing Animal by R-Gel 200 μL of the Cy7-R-Gel or Cy7-animal gelatin produced in (6) above was administered to the cancer-bearing animal produced in (9) above via caudal vein administration, and a fluorescence imaging experiment was then carried out from the outside of the body of the animal.

For detection of a fluorescence signal, measurement, and imaging, Lumino image analyzer LAS5000 (a trial product of Fujifilm Corporation) was used. A visible light image and a fluorescence image were simultaneously taken, and the two images were then overlapped to identify a site from which fluorescence was emitted. In order to take such a fluorescence image, indicent light-IR light source was used as a light source, and a 785-nm band-pass filter was used as a filter. For image analysis and quantification of signal strength, software, MultiGauge (Fujifilm Corporation) was used.

Figure 9:
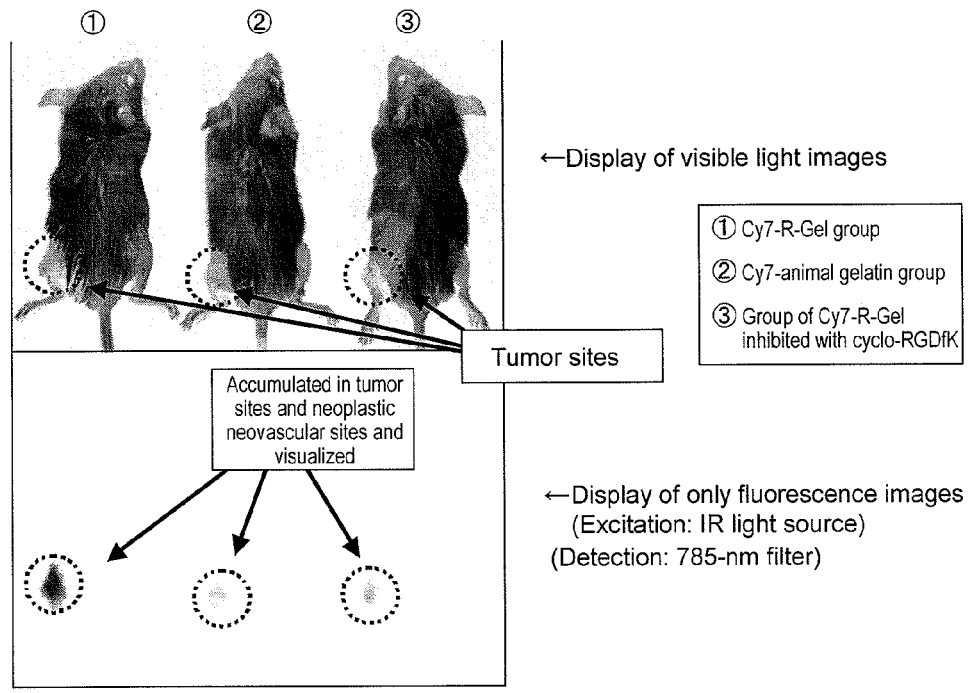
FIG. 9 shows the imaging of tumor sites and neoplastic neovascular sites in cancer-bearing animals.

As a result, using Cy7-R-Gel and Cy7-animal gelatin, the inventors succeeded in imaging the tumoral neovascular site and tumor site of a cancer-bearing animal from the outside of the body (FIG. 9). (It is possible that the visible light image and the fluorescence image are displayed by overlapping them and each fluorescence intensity is color-coded. However, since black-and-white images were used in the present specification, the visible light image and the fluorescence image were displayed, separately.) Moreover, Cy7-R-Gel accumulated in the tumor site and the tumoral neovascular site at a level significantly higher than that of Cy7-animal gelatin.

Figure 10:
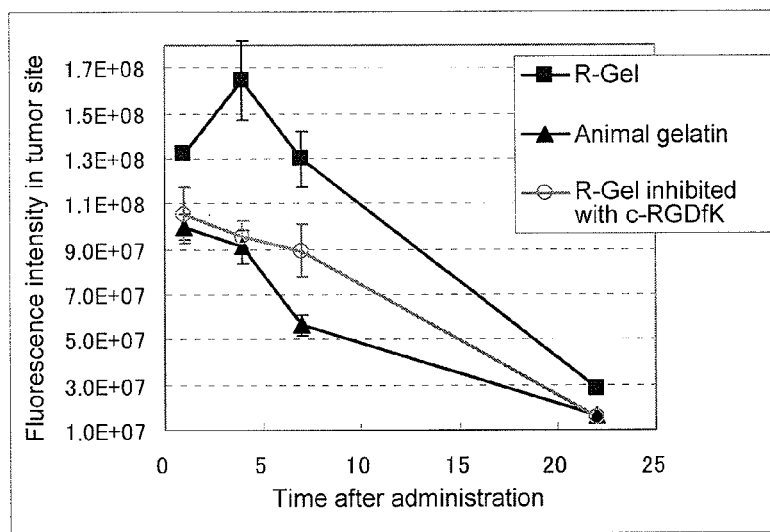
FIG. 10 shows accumulation in tumor and neoplastic neovascular sites.

At the same time, in the same manner as that applied in the Example of (8) above, a sufficient amount of cyclo-RGDfK had previously been administered to the present cancer-bearing animal before administration of Cy7-R-Gel, and thirty minutes later, Cy7-R-Gel was administered to the animal, and an imaging experiment was then carried out. As a result, as shown in FIG. 9 and FIG. 10, accumulation of R-Gel in the tumoral neovascular site and the tumor site was decreased.

(11) Cell Adhesiveness Test (for Interaction Between R-Gel and αVβ3 integrin)

In order to elucidate the mechanism of R-Gel to cause accumulation of newly formed blood vessels, tests were conducted to examine cell adhesiveness of R-Gel to vascular endothelial cells and experiments were conducted to examine interaction between R-Gel and αVβ3 integrin.

HUVECs (normal human umbilical vein endothelial cells; Takara Bio Inc.) were used as vascular endothelial cells. It is known that many αVβ3 integrin molecules are permanently expressed on the surfaces of HUVECs. By testing cell adhesiveness of R-Gel to HUVECs, binding of R-Gel to vascular endothelial cells activated by newly formed blood vessels can be elucidated. Also, binding of R-Gel to αVβ3 integrin that has been reported to be highly expressed at newly formed blood vessel sites can be elucidated.

For culture of HUVECs, endothelial cell basic medium-2 (containing no serum) (EBM™-2) and endothelial cell medium kit-2 (2% FBS) (EGM™-2 BulletKit™) were used (Takara Bio Inc.). Upon subculture and removal of cells, an EDTA-containing 0.25% trypsin solution was used. HUVECs that had been allowed to proliferate to a sufficient amount in a T-75 flask were removed from the bottom surface of the flask, followed by centrifugation for removal of the supernatant. Then, the resultant was washed with the above endothelial cell basic medium-2 containing the endothelial cell medium kit 2. Centrifugation was performed again to remove the supernatant. A solution obtained by adding 0.1% BSA to endothelial cell basic medium-2 containing no endothelial cell medium kit 2 was added thereto for suspension. The number of living cells was counted using cell counter. The final cell concentration was adjusted to 500,000 cells/mL.

Meanwhile, plates coated with various proteins (R-Gel, fibronectin, collagen manufactured by Fibrogen (hereinafter referred to as "Fibrogen"), pig skin gelatin (hereinafter referred to as "PSK"), and beef-bone-derived gelatin (hereinafter referred to as "G1917P")) were prepared for cell adhesiveness tests. R-Gel was dissolved in PBS (phosphate buffer) at a concentration of 1 mg/mL to prepare an R-Gel solution. Fibronectin was dissolved in PBS (phosphate buffer) at a concentration of 1 mg/mL to prepare a fibronectin solution. Fibrogen was dissolved in PBS (phosphate buffer) at a concentration of 1 mg/mL to prepare a fibrogen solution. PSK was dissolved in PBS (phosphate buffer) at a concentration of 1 mg/mL to prepare a PSK solution. G1917P was dissolved in PBS (phosphate buffer) at a concentration of 1 mg/mL to prepare a G1917P solution. The above solutions were diluted with PBS according to need and used as solutions to be added to plates.

Non-treated 96-well plates (IWAKI) were used as plates. Solutions obtained by diluting the above lysates with PBS were added to non-treated 96-well plates (50 μL/well) so as to result in protein concentrations of 0.02, 0.1, 0.2, and 2.0 μg/well. Then, incubation was carried out at 37° C. for 2 hours. After removal of each solution, PBS (100 μL) was added to every well, followed by washing for removal of PBS (a washing step). The washing step was repeated 3 times. Accordingly, plates coated with different coating proteins at different coating concentrations were obtained.

The HUVEC suspension (500,000 cells/mL) prepared above was seeded on the coating plates (100 μL each), followed by incubation at 37° C. for 1 hour. Then, the medium was removed by suction, followed by washing with PBS (100 μL). PBS was removed by suction (PBS washing). PBS washing was repeated 3 times in the above manner. Thus, the plates from which PBS had been removed were obtained.

DNA assay was performed for quantitative determination of the number of cells on the obtained plates. 100 μl of an SDS solution (i.e., a solution obtained by dissolving 20 mg of SDS in 100 mL of a 1×SSC solution (obtained by dissolving 17.999 g of NaCl and 8.823 g of Na$_3$-citrate in 2 L of ultrapure water)) was added to each of wells of the obtained plates. Each plate was allowed to stand still at 37° C. for 1 hour. The total amount of each obtained solution was transferred to a 96-well black plate (Non-treated) and 100 μL, of a Hoechst solution (obtained by mixing 20 μl of Hoechst 33258 with 20 mL of a 1×SSC solution) was added to every well, followed by determination of the fluorescence intensity using a plate reader. The fluorescence intensity was measured using a Gemini EM plate reader (Molecular Devices Corporation) at an excitation wavelength of 355 nm and a measurement wavelength of 460 nm. A calibration curve was created using a suspension containing HUVECs at the adjusted number of cells.

Figure 11:
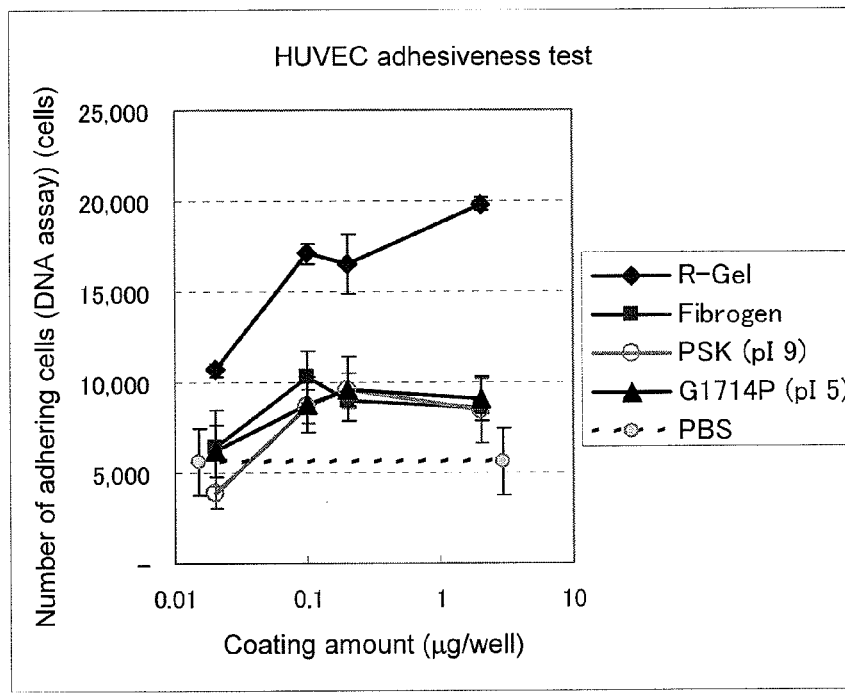
FIG. 11 shows the results of an HUVEC cell adhesiveness test.
Figure 12:
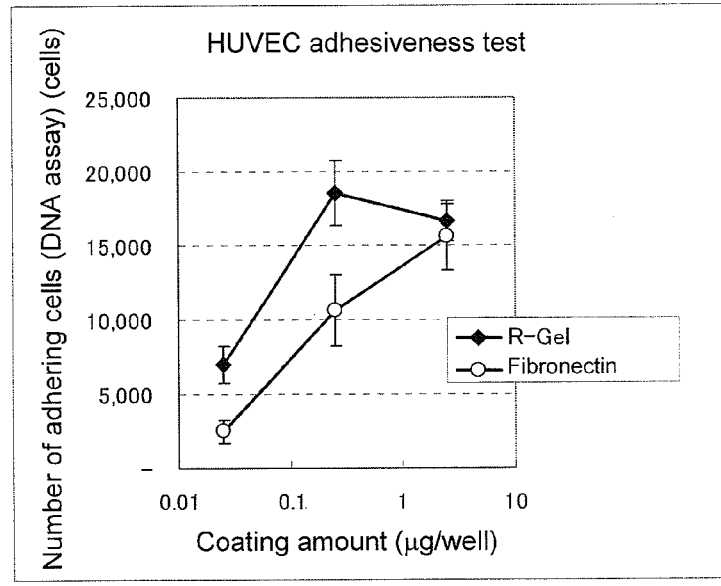
FIG. 12 shows the results of an HUVEC cell adhesiveness test.
Figure 13:
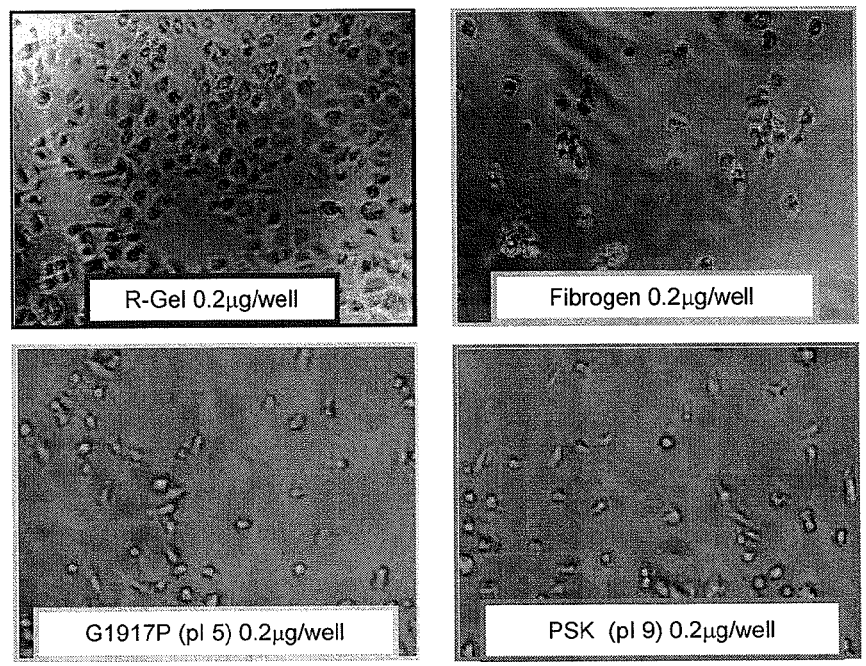
FIG. 13 shows photos of HUVECs on plates coated with various types of proteins.
Figure 14:
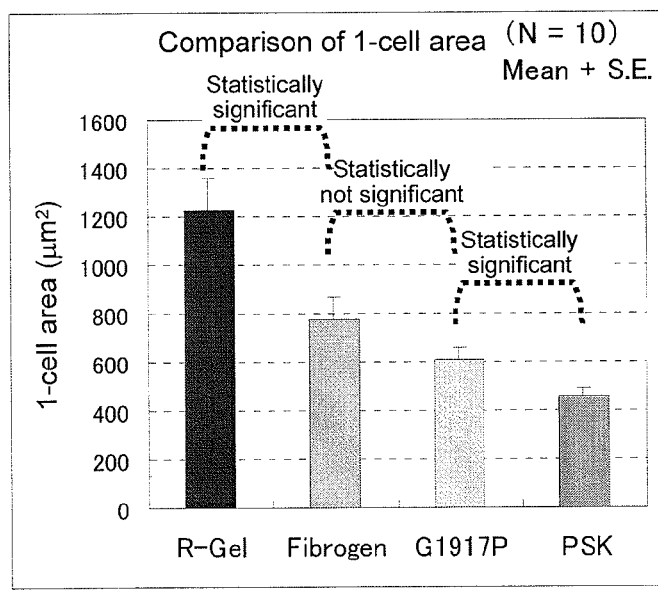
FIG. 14 shows comparison of a 1-cell area for HUVEC cells on plates coated with various types of proteins.

FIGS. 11 and 12 show the obtained results of cell adhesiveness tests (by DNA assay). The results showed that R-Gel is superior to fibronectin, Fibrogen, PSK, and G1917P in terms of adhesion to HUVECs. In addition, FIG. 13 shows a photo of cell adhesion on the R-Gel-coated plate, a photo of cell adhesion on the Fibrogen-coated plate, a photo of cell adhesion on the PSK-coated plate, and a photo of cell adhesion on the G1917P-coated plate. It can be visually confirmed that the largest number of cells adhered to the R-Gel-coated plate. At the same time, the area of a single cell separately adhering to a plate was determined based on the photos using the ImageJ software. FIG. 14 shows the results. The results showed that R-Gel is significantly superior to Fibrogen, PSK, and G1917P in terms of 1-cell area. Therefore, it was found that binding between R-Gel and HUVECs takes place more strongly than binding in the other cases.

(12) Experimentation of Inhibition of αVβ3-Integrin-Mediated HUVEC Adhesion

In order to identify binding between R-Gel and HUVECs as αVβ3-integrin-mediated binding, experimentation was conducted to determine whether or not R-Gel-to-cell adhesion would be inhibited by blocking αVβ3 integrin with an anti-αV antibody in the R-Gel-to-cell adhesiveness tests conducted in (7) above.

Specifically, cell adhesion experiments were conducted as described in (7) above. Experiments were conducted using the R-Gel-coated plate and the fibronectin-coated plate at a coating concentration of 0.2 μg/well. The prepared HUVECs were incubated with anti-human αV monoclonal antibodies (MAB1980: CHEMICON) at a sufficient concentration at 37° C. for 30 minutes, and they are described as "antibody-treated HUVECs". On the other hand, the prepared HUVECs were incubated with the addition of the same amount of PBS at 37° C. for 30 minutes, and they are described as ""untreated HUVECs". Cells were inoculated on plates with addition of a solution (100 μL/well) prepared in a manner such that it contained antibody-treated HUVECs or untreated HUVECs at a concentration of 1,000,000 cells/mL. The time for cell adhesion was determined to be 1 hour at 37° C. as in the case of (7) above. Quantitative determination of the number of cells was carried out by DNA assay as in the case of (7) above.

Figure 15:
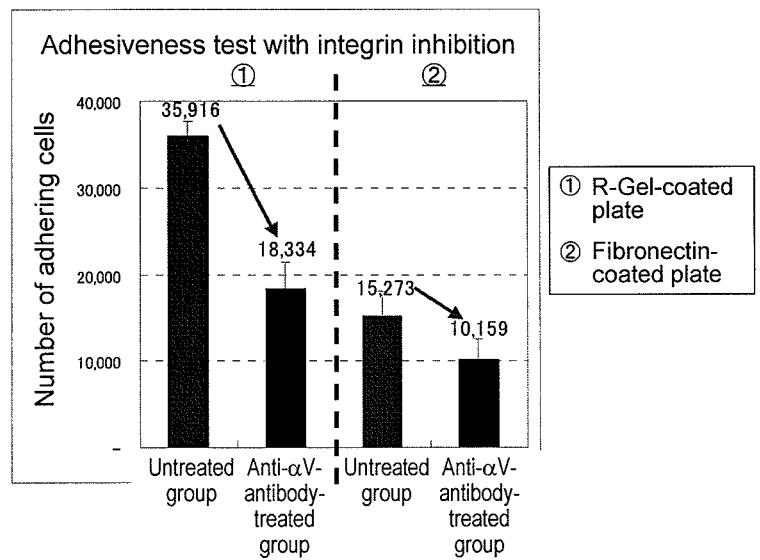
FIG. 15 shows inhibition of HUVEC adhesion caused by an anti-αV antibody.

The obtained results are shown in FIG. 15. The results showed that adhesion of R-Gel and fibronectin to HUVECs is significantly inhibited by an anti-human αV antibody. It is known that fibronectin binds to HUVECs via αVβ3 integrin. In this Example, it was shown that R-Gel also binds to HUVECs via αVβ3 integrin as in the case of fibronectin.

This indicates that R-Gel binds to αVβ3 integrin. The results obtained in (7) and (8) above indicate that R-Gel binds to αVβ3 integrin with good efficiency and the binding is stronger than binding in the cases of other collagens/gelatins, and that R-Gel binds to vascular endothelial cells with good efficiency and the binding is stronger than binding in the cases of other collagens/gelatins. That is, the results showed R-Gel has a high ability to bind to newly formed vessels in a highly specific manner at cellular/molecular levels.

The invention claimed is:

1. A method for targeting a substance to a neovascular site, which comprises administering a recombinant gelatin to a subject,
wherein the recombinant gelatin has the following (1) or (2):
(1) the amino acid sequence shown in SEQ ID NO: 1; or
(2) an amino acid sequence having 80% or more percent identity to the amino acid sequence shown in SEQ ID NO: 1 and having an action to accumulate in newly formed blood vessels,
and wherein the recombinant gelatin is used in combination with a labeled probe, the labeled probe being selected from the group consisting of a fluorescent dye, a radioisotope, a nuclide used for PET, a nuclide used for SPECT, an MRI contrast medium, a CT contrast medium, and a magnetic material.

2. The method according to claim 1, further comprising imaging a neovascular site in said subject.

3. The method according to claim 1, wherein a drug is present in combination with the recombinant gelatin and the labeled probe.

4. The method according to claim 1, wherein the recombinant gelatin has a molecular weight of 2 KDa to 100 KDa.

5. The method according to claim 1, wherein the recombinant gelatin has a molecular weight of 10 KDa to 90 KDa.

6. The method according to claim 1, wherein the amino acid sequence of the recombinant gelatin does not comprise any of serine and threonine.

7. The method according to claim 1, wherein the recombinant gelatin is crosslinked.

8. The method according to claim 7, wherein the crosslinking is carried out using an aldehyde, condensing agent, or enzyme.

9. The method according to claim 1, wherein the fluorescent dye is a quantum dot, indocyanine green, or a near-infrared fluorescent dye; each of the radioisotope, the nuclide used for PET, and the nuclide used for SPECT is $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, or a complex thereof, or a combination thereof; and each of the MRI contrast medium, the CT contrast medium, and the magnetic material is gadolinium, Gd-DTPA, Gd-DTPA-BMA, Gd-HP-DO3A, iodine, iron, iron oxide, chromium, manganese, a complex or chelate complex thereof, or a combination thereof.

10. The method according to claim 1, wherein the recombinant gelatin is physically or chemically bound to the labeled probe, directly or via a linker.

11. The method according to claim 10, wherein the bond is a coordinate bond, a covalent bond, a hydrogen bond, hydrophobic interaction, or physical adsorption.

* * * * *

SEQUENCE LISTING

```
<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270
```

-continued

Asp Gly Val Arg Gly Leu Ala Gly Pro Ile Gly Pro Pro Gly Glu Arg
            275                 280                 285

Gly Ala Ala Gly Leu Pro Gly Pro Lys Gly Glu Arg Gly Asp Ala Gly
        290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
    370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Ala Gly Pro Lys Gly Ala Asp Gly Ala Pro Gly Lys Asp Gly Val
    450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
    530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Asp Arg Gly Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Arg Glu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Tyr Ile Gly Ser Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 5

Pro Asp Ser Gly Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Arg Tyr Val Val Leu Pro Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 7

Leu Gly Thr Ile Pro Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 8

Arg Asn Ile Ala Glu Ile Ile Lys Asp Ile
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

```
Ile Lys Val Ala Val
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Glu Arg Gly Asp
1
```